United States Patent
Downer

(10) Patent No.: US 9,522,061 B2
(45) Date of Patent: Dec. 20, 2016

(54) LENS DELIVERY SYSTEM

(75) Inventor: David A. Downer, Fort Worth, TX (US)

(73) Assignee: Novartis AG, Basel (CH)

(*) Notice: Subject to any disclaimer, the term of this patent is extended or adjusted under 35 U.S.C. 154(b) by 1634 days.

(21) Appl. No.: 11/675,380

(22) Filed: Feb. 15, 2007

(65) Prior Publication Data
US 2008/0200920 A1 Aug. 21, 2008

(51) Int. Cl.
*A61F 2/16* (2006.01)

(52) U.S. Cl.
CPC ............ *A61F 2/1678* (2013.01); *A61F 2/167* (2013.01)

(58) Field of Classification Search
CPC ...... A61F 2/1678; A61F 2/167; A61F 2/1667; A61F 2/1672
USPC ...... 623/6.12, 907, 6.11; 606/184, 107, 108, 606/171, 167, 127, 128, 110–115, 170; 604/68, 71, 64, 246, 232, 57, 29, 60, 208, 604/221, 218, 227, 228, 315, 314, 335, 604/162; 600/3–8; 30/315, 314, 335, 162
See application file for complete search history.

(56) References Cited

U.S. PATENT DOCUMENTS

| | | | |
|---|---|---|---|
| 4,681,102 A | 7/1987 | Bartell | |
| 5,026,396 A | 6/1991 | Darin | |
| 5,098,439 A * | 3/1992 | Hill et al. | 606/107 |
| 5,190,552 A * | 3/1993 | Kelman | 606/107 |
| 5,275,604 A | 1/1994 | Rheinish et al. | |
| 5,304,182 A | 4/1994 | Rheinish et al. | |
| 5,494,484 A | 2/1996 | Feingold | |
| 5,499,987 A | 3/1996 | Feingold | |
| 5,578,042 A | 11/1996 | Cumming | |
| 5,616,148 A | 4/1997 | Eagles et al. | |
| 5,620,450 A | 4/1997 | Eagles et al. | |
| 5,653,715 A | 8/1997 | Reich et al. | |
| 5,716,364 A | 2/1998 | Makker et al. | |
| 5,776,138 A * | 7/1998 | Vidal et al. | 606/107 |
| 5,820,373 A | 10/1998 | Okano et al. | |
| 6,010,510 A | 1/2000 | Brown et al. | |
| 6,056,757 A * | 5/2000 | Feingold et al. | 606/107 |
| 6,162,230 A | 12/2000 | Polla et al. | |
| 6,163,963 A * | 12/2000 | Huang | 30/162 |
| 6,228,094 B1 | 5/2001 | Erdman | |
| 6,276,014 B1 * | 8/2001 | Lee | 7/158 |
| 6,447,519 B1 | 9/2002 | Brady et al. | |
| 6,471,708 B2 | 10/2002 | Green | |
| 6,500,181 B1 | 12/2002 | Portney | |
| 6,607,537 B1 * | 8/2003 | Binder | 606/107 |
| 6,685,740 B2 | 2/2004 | Figueroa et al. | |
| 6,899,717 B2 * | 5/2005 | Weber et al. | 606/107 |
| 6,964,648 B2 * | 11/2005 | Talling et al. | 604/60 |
| 7,131,976 B2 * | 11/2006 | Kobayashi et al. | 606/107 |
| 7,156,854 B2 | 1/2007 | Brown et al. | |
| 7,189,218 B2 * | 3/2007 | Lichtenberg | 604/187 |
| 7,422,604 B2 | 9/2008 | Vaquero et al. | |

(Continued)

FOREIGN PATENT DOCUMENTS

| | | |
|---|---|---|
| EP | 0174917 A1 | 3/1986 |
| EP | 1360944 A2 | 11/2003 |

(Continued)

OTHER PUBLICATIONS

Barakova D., abstract of "Implantation of the AcrySof MA3OBA Lens Using the Monarch System," found in PubMed database, May 2002, http://ncbi.nlm.gov/pubmed/12087658 (1 page).

*Primary Examiner* — Jocelin Tanner

(57) ABSTRACT

A lens delivery system having a plunger rod with a sliding block reinforcing member. The sliding block rides on and along with the plunger rod and helps to reinforce the plunger rod against bending or buckling during use.

20 Claims, 3 Drawing Sheets

(56) References Cited

U.S. PATENT DOCUMENTS

| | | |
|---|---|---|
| 7,429,263 B2 | 9/2008 | Vaquero et al. |
| 2003/0135221 A1* | 7/2003 | Sabet ............................ 606/107 |
| 2003/0212406 A1 | 11/2003 | Kobayashi et al. |
| 2003/0212409 A1 | 11/2003 | Kobayashi et al. |
| 2004/0054374 A1 | 3/2004 | Weber et al. |
| 2004/0087896 A1* | 5/2004 | Wise et al. ....................... 604/68 |
| 2004/0160575 A1 | 8/2004 | Ayton et al. |
| 2004/0238392 A1 | 12/2004 | Peterson et al. |
| 2005/0049605 A1 | 3/2005 | Vaquero et al. |
| 2005/0049606 A1 | 3/2005 | Vaquero et al. |
| 2005/0143750 A1 | 6/2005 | Vaquero |
| 2005/0149056 A1 | 7/2005 | Rathert |
| 2005/0203619 A1 | 9/2005 | Altmann |
| 2005/0222578 A1 | 10/2005 | Vaquero |
| 2005/0222579 A1 | 10/2005 | Vaquero et al. |
| 2006/0063962 A1 | 3/2006 | Drobnik et al. |
| 2006/0184181 A1 | 8/2006 | Cole et al. |
| 2006/0200167 A1 | 9/2006 | Peterson et al. |
| 2006/0229634 A1* | 10/2006 | Shepherd ....................... 606/107 |
| 2007/0050023 A1 | 3/2007 | Bessiere et al. |
| 2007/0060925 A1 | 3/2007 | Pynson |
| 2007/0173860 A1 | 7/2007 | Iwaski |
| 2008/0039862 A1 | 2/2008 | Tran |
| 2008/0200921 A1 | 8/2008 | Downer |
| 2008/0221584 A1 | 9/2008 | Downer |
| 2008/0221585 A1 | 9/2008 | Downer |
| 2008/0255577 A1 | 10/2008 | Downer |
| 2009/0043313 A1 | 2/2009 | Ichinohe et al. |
| 2009/0112223 A1 | 4/2009 | Downer |
| 2009/0171366 A1 | 7/2009 | Tanaka |
| 2009/0204123 A1 | 8/2009 | Downer |

FOREIGN PATENT DOCUMENTS

| | | |
|---|---|---|
| EP | 1481652 A1 | 12/2004 |
| EP | 1661533 A1 | 5/2006 |
| EP | 1849436 A1 | 10/2007 |
| EP | 1891911 A1 | 2/2008 |
| EP | 1958593 A1 | 8/2008 |
| EP | 2062552 A1 | 5/2009 |
| FR | 2820633 | 8/2002 |
| JP | 2003070829 A | 3/2003 |
| JP | 2003325569 A | 11/2003 |
| JP | 2006181269 | 7/2006 |
| RU | 2138232 C1 | 9/1999 |
| RU | 2238283 C2 | 10/2004 |
| RU | 2242956 C1 | 12/2004 |
| SU | 1440496 A1 | 11/1988 |
| WO | WO 94/07436 A1 | 4/1994 |
| WO | WO 96/10372 A1 | 4/1996 |
| WO | WO 98/20819 A1 | 5/1998 |
| WO | WO 00/40175 | 7/2000 |
| WO | WO 2005/023154 A2 | 3/2005 |
| WO | WO 2005/023154 A3 | 3/2005 |
| WO | WO 2005/102223 A1 | 11/2005 |
| WO | WO 2006/059183 | 6/2006 |
| WO | WO 2006/070561 A1 | 7/2006 |
| WO | WO 2006/080191 A1 | 8/2006 |
| WO | WO 2006/113138 A1 | 10/2006 |
| WO | WO 2006/113357 A2 | 10/2006 |

\* cited by examiner

LENS DELIVERY SYSTEM

This invention relates to intraocular lenses (IOLs) and more particularly to devices used to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. One of the most commonly used injector cartridge design is illustrated in U.S. Pat. No. 4,681,102 (Bartell), and includes a split, longitudinally hinged cartridge. Another recently introduced disposable lens delivery system is disclosed in U.S. Pat. No. 7,156,854 B2 (Brown, et al.). Other cartridge designs are illustrated in U.S. Pat. Nos. 5,494,484 and 5,499,987 (Feingold) and U.S. Pat. Nos. 5,616,148 and 5,620,450 (Eagles, et al.). In an attempt to avoid the claims of U.S. Pat. No. 4,681,102, several solid cartridges have been investigated, see for example U.S. Pat. No. 5,275,604 (Rheinish, et al.) and U.S. Pat. No. 5,653,715 (Reich, et al.).

The ability to express a lens out of a cartridge without damage is dependent on lens design and material. Silicone lenses, being made from a relatively rugged and durable material, can be compressed more aggressively. High water content hydrogel material, being more fragile, must be folded more gently. Soft acrylics, being viscoelastic in nature, are highly sensitive to temperature, and can be brittle if too cold, and can be unworkable if too warm. Soft acrylics, when compressed at an appropriate temperature, can be described as "flowing" rather than folding. For this reason, soft acrylics are best compressed slowly and in a very controlled manner.

Prior art lens delivery handpiece suitable for use with soft acrylic IOLs generally have plungers with very long plunger rods. The long stroke on these handpieces causes the lens to be folded more slowly as the lens is pushed down the relatively long length of the folding cartridge. As preferred incision sizes have gotten smaller, the diameter of the cartridge nozzle has also gotten smaller, forcing the lens to be compressed much more tightly than in the past. The force require to push the lens down the cartridge nozzle has increased correspondingly. This increase force on the plunger rod can cause the plunger rod to buckle or bend.

Accordingly, a need continues to exist for a device to help prevent bending or buckling of a lens delivery handpiece plunge rod during use.

BRIEF SUMMARY OF THE INVENTION

The present invention improves upon prior art by providing a lens delivery system having a plunger rod with a sliding block reinforcing member. The sliding block rides on and along with the plunger rod and helps to reinforce the plunger rod against bending or buckling during use.

It is accordingly an objective of the present invention to provide a lens delivery system that is suitable for folding lenses made from a soft acrylic material.

It is a further objective of the present invention to provide a lens delivery system having a sliding block.

It is a further objective of the present invention to provide a lens delivery system having a device for helping to resist bending and buckling of the plunger rod.

Other objectives, features and advantages of the present invention will become apparent with reference to the drawings, and the following description of the drawings and claims.

DETAILED DESCRIPTION OF THE PREFERRED EMBODIMENTS

Figure 1:
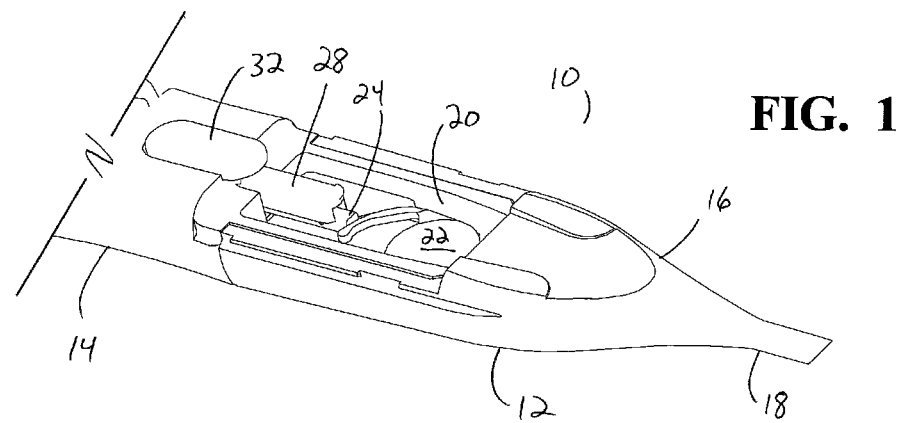
FIG. 1 is an enlarged partial perspective view of the distal end of the lens delivery handpiece or system of the present invention.
Figure 6:
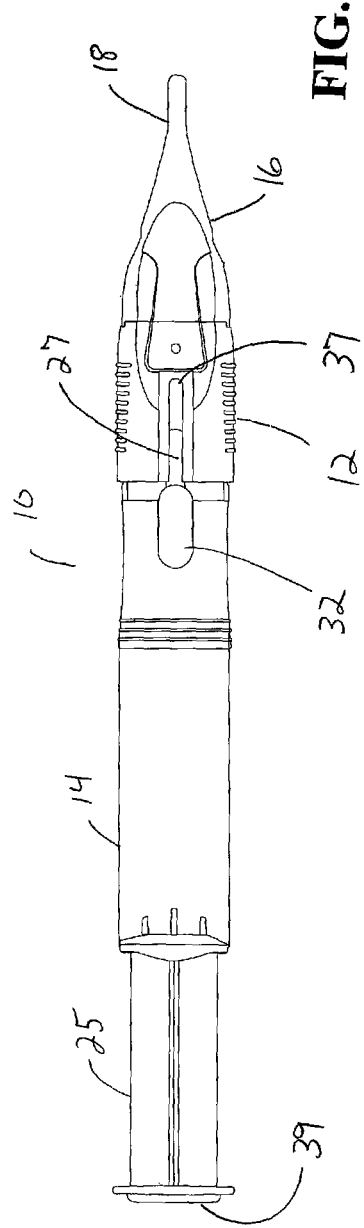
FIG. 6 is a top plane view of the lens delivery system of the present invention.

As best seen in FIGS. 1 and 6, lens delivery system 10 of the present invention generally includes cartridge 12 and handpiece 14. As best seen in FIG. 1 cartridge 12 generally has tubular body 16 and injection nozzle 18. Cartridge 12 is molded as a single piece from any suitable thermoplastic, such as polypropylene, and the thermoplastic may contain a lubricity enhancing agent such as those disclosed in U.S. Pat. No. 5,716,364, the entire contents of which are incorporated herein by reference. Alternatively, cartridge 12 may be integrally formed with handpiece 14. Nozzle 18 preferably is round, oval or elliptical in cross-section and has a cross-sectional area of between around 1.0 mm$^2$ to around 2.6 mm$^2$. Cartridge 12 contains chamber 20 for receiving lens 22 to be folded. Lens 22 is pushed out of chamber 20 and down nozzle 18 by plunger rod 24 in a manner well-known in the art.

Figure 3:
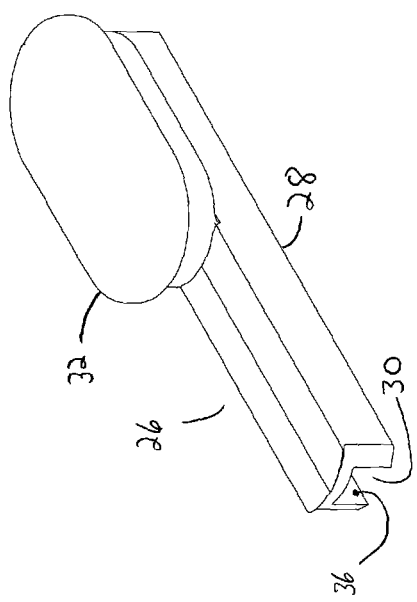
FIG. 3 is an enlarged partial perspective view of the sliding block of the present invention.
Figure 4:
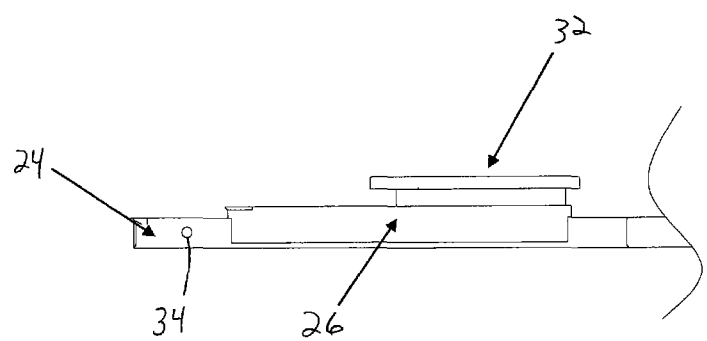
FIG. 4 is an enlarged side elevational view of the sliding block of the present invention installed on a plunger rod.
Figure 5:
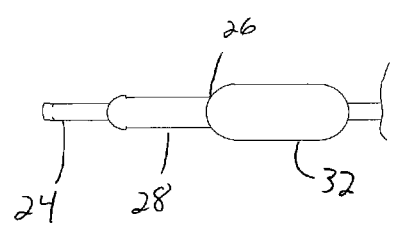
FIG. 5 is an enlarged top plan view of the sliding block of the present invention installed on a plunger rod.

As best seen in FIGS. 3, 4 and 5, sliding block 26 that may be used with the lens delivery system of the present invention generally consists of elongated body 28 having channel or groove 30 and actuation button 32. Groove 30 is sized and shaped to fit over and slide upon plunger rod 24. Plunger rod 24 is attached to, and extends distally from, plunger 25 and contains detents 34 that engage pins 36 contained within groove 30 so that movement of sliding block 26 within slot 27 of cartridge 12 also causes movement of plunger rod 24 and plunger 25, as will be described below.

Figure 2:
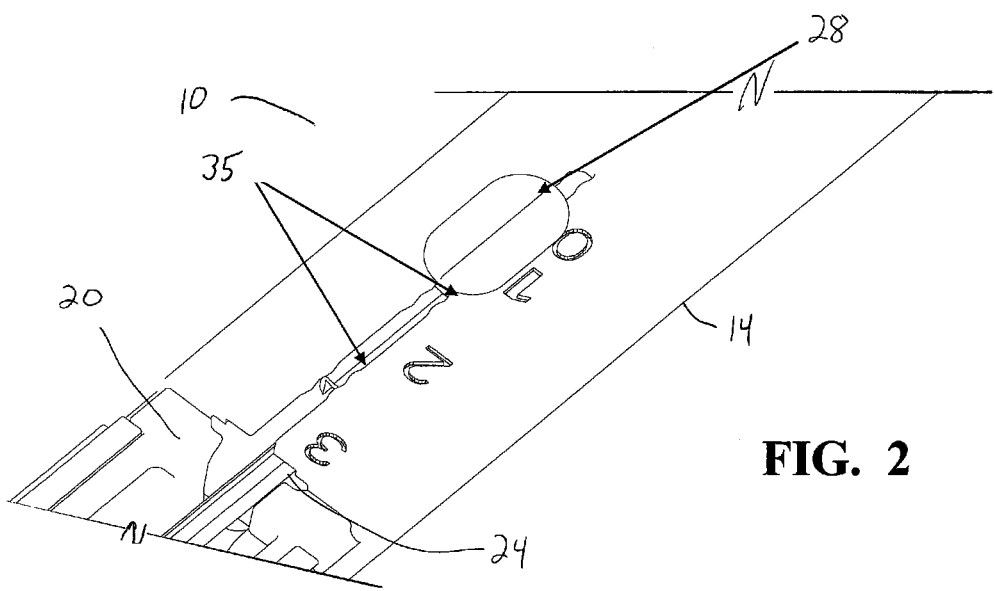
FIG. 2 is an enlarged partial perspective view of the sliding block installed on lens delivery handpiece or system of the present invention.

In use, plunger 25 is pulled proximally (away from nozzle 18) so that plunger rod 24 and sliding block 26 are retracted within handpiece 14 exposing chamber 20 allowing lens 22 to be placed in chamber 20 as seen in FIGS. 1, 2 and 6. Sliding block 26 is advanced forward by pushing actuation button 32 distally to one of multiple, pre-measured desirable distances (graduation marks 1, 2 and 3 in FIG. 2). Movement of sliding block 26 also causes movement of plunger rod 24 because of the interlocking arrangement of detents 34 and pins 36. As sliding block 26 is pushed distally, a series of staging detent stops 35 may be provided so as to indicate to the user a particular stage of the lens delivery process. Sliding block 26 may in continued to be pushed distally until button 32 reaches distal end 37 of slot 27, thereby preventing any further movement of sliding block 26, as indicated in FIG. 1. Further movement of plunger rod 24 is accomplished by pressing on end cap 39 of plunger 25, which causes plunger rod 24 to overcome the holding force of detents 34 and pins 36 to push lens 22 distally out of chamber 20, through cartridge 12 and out nozzle 18. During this further movement of plunger rod 24, body 28 of sliding block 26 acts as a stiffener, helping to reduce bending and buckling of plunger rod 24.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An intraocular lens delivery system, comprising:
   a) a cartridge comprising a slot;
   b) a tubular handpiece having an interior wall;
   c) a plunger having an attached distally extending plunger rod, the plunger being sized and shaped to reciprocate within the tubular handpiece; and
   d) a sliding block having a groove, the groove sized and shaped to fit over the plunger rod;
   wherein forward movement of the sliding block within the slot of the cartridge also causes movement of the plunger rod and plunger, wherein the sliding block is frictionally engaged with the plunger rod so that movement of the sliding block causes movement of the plunger rod;
   wherein the sliding block is configured to be pushed forward until a button on the sliding block reaches a distal end of the slot configured to limit travel of the sliding block;
   wherein further forward movement of the plunger rod after the sliding block reaches the distal end of the slot is accomplished by pressing on an end cap of the plunger;
   wherein during the further movement of the plunger rod, the sliding block acts as a stiffener to reduce bending and buckling of the plunger rod.

2. The lens delivery system of claim 1, wherein the distal end of the slot does not limit the travel of the plunger rod.

3. The lens delivery system of claim 1, wherein the cartridge is coupled to the handpiece and comprises a chamber for receiving an unfolded lens to be delivered.

4. The lens delivery system of claim 1, wherein the plunger rod and the sliding block groove comprise corresponding detents and pins so that movement of the sliding block causes movement of the plunger rod through at least a portion of the plunger rod movement to deliver a lens.

5. The lens delivery system of claim 1,
   wherein a portion of the sliding block configured to move within the slot comprises an actuation button;
   wherein the sliding block is configured to be moved by pushing the actuation button distally; and
   wherein the sliding block is configured to be pushed forward until the actuation button reaches the distal end of the slot.

6. The lens delivery system of claim 5, wherein the sliding block is configured to engage a series of staging detent stops as the sliding block is pushed forward.

7. The intraocular lens delivery system of claim 1, wherein the plunger is configured to be pulled proximally away from a nozzle so that the plunger rod and sliding block are retracted within the handpiece to expose a chamber to allow a lens to be placed into the chamber.

8. The intraocular lens delivery system of claim 1, wherein the sliding block is configured to be advanced forward by pushing the button on the sliding block distally to one of multiple, pre-measured desirable distances indicated by graduation marks.

9. The intraocular lens delivery system of claim 1, wherein the groove of the sliding block comprises a rectangular cross section and is configured to contact the plunger rod on two opposite sides of the plunger rod.

10. An intraocular lens delivery system, comprising:
    a) a cartridge;
    b) a tubular handpiece having an interior wall;
    c) a plunger having an attached distally extending plunger rod, the plunger being sized and shaped to reciprocate within the tubular handpiece; and
    d) a sliding block having a groove, the groove sized and shaped to fit over the plunger rod and reciprocate within a slot in the cartridge, the slot having a distal end limiting travel of the sliding block;
    wherein movement of the sliding block within the slot of the cartridge also causes movement of the plunger rod and plunger, wherein the sliding block is frictionally engaged with the plunger rod so that movement of the sliding block causes movement of the plunger rod;
    wherein as the sliding block is pushed forward, a series of staging detent stops indicate to a user a particular stage of a lens delivery process;
    wherein the sliding block is configured to be pushed forward until a button on the sliding block reaches the distal end of the slot configured to limit travel of the sliding block;
    wherein further forward movement of the plunger rod after the sliding block reaches the distal end of the slot is accomplished by pressing on an end cap of the plunger;
    wherein during the further forward movement of the plunger rod after the sliding block reaches the distal end of the slot, the sliding block acts as a stiffener to reduce bending and buckling of the plunger rod.

11. The lens delivery system of claim 10, further comprising:
    a nozzle coupled to the cartridge, wherein the plunger rod is configured to push a lens through the nozzle.

12. The intraocular lens delivery system of claim 10, wherein the plunger is configured to be pulled proximally away from a nozzle, and wherein movement of the plunger away from the nozzle causes the plunger rod and sliding block to be retracted within the handpiece to expose a chamber to allow a lens to be placed into the chamber.

13. The intraocular lens delivery system of claim 10, wherein the sliding block is configured to be advanced forward by pushing the button on the sliding block distally to one of multiple, pre-measured desirable distances indicated by graduation marks.

14. The intraocular lens delivery system of claim 10, wherein the plunger rod and the sliding block groove comprise corresponding detents and pins so that movement of the sliding block causes movement of the plunger rod through at least a portion of the plunger rod movement to deliver a lens.

15. An intraocular lens delivery system, comprising:
a cartridge comprising a slot;
a tubular handpiece;
a plunger comprising a plunger rod, the plunger configured to reciprocate within the tubular handpiece; and
a sliding block having a groove, the groove configured to fit over the plunger rod;
wherein movement of the sliding block within the slot of the cartridge also causes movement of the plunger rod and plunger, wherein the sliding block is frictionally engaged with the plunger rod so that movement of the sliding block causes movement of the plunger rod;
wherein the sliding block is configured to be pushed forward until a button on the sliding block reaches a distal end of the slot configured to limit travel of the sliding block;
wherein further forward movement of the plunger rod after the sliding block reaches the distal end of the slot is accomplished by pressing on an end cap of the plunger;
wherein during the further forward movement of the plunger rod after the sliding block reaches the distal end of the slot, the sliding block acts as a stiffener to reduce bending and buckling of the plunger rod.

16. The lens delivery system of claim 15, wherein the cartridge comprises a chamber for receiving an unfolded lens to be delivered.

17. The lens delivery system of claim 15, wherein the plunger rod and the sliding block groove comprise corresponding detents and pins so that movement of the sliding block causes movement of the plunger rod through at least a portion of the plunger rod movement to deliver a lens.

18. The lens delivery system of claim 15, wherein the sliding block is configured to engage a series of staging detent stops as the sliding block is pushed forward.

19. The intraocular lens delivery system of claim 15, wherein the plunger is configured to be pulled proximally away from a nozzle, and wherein movement of the plunger away from the nozzle causes the plunger rod and sliding block to be retracted within the handpiece to expose a chamber to allow a lens to be placed into the chamber.

20. The intraocular lens delivery system of claim 15, wherein the sliding block is configured to be advanced forward by pushing the button on the sliding block distally to one of multiple, pre-measured desirable distances indicated by graduation marks.

* * * * *